(12) United States Patent
Birlouez et al.

(10) Patent No.: US 9,933,361 B2
(45) Date of Patent: Apr. 3, 2018

(54) METHOD FOR ESTIMATING DENATURED SERUM PROTEINS IN MILK

(71) Applicant: SPECTRALYS INNOVATION, Romainville (FR)

(72) Inventors: Inès Birlouez, Ermont (FR); Pierre Lacotte, Beziers (FR); Abdelhaq Acharid, Arnouville (FR)

(73) Assignee: SPECTRALYS INNOVATION, Romainville (FR)

( * ) Notice: Subject to any disclaimer, the term of this patent is extended or adjusted under 35 U.S.C. 154(b) by 0 days.

(21) Appl. No.: 15/129,784

(22) PCT Filed: Mar. 25, 2015

(86) PCT No.: PCT/IB2015/052196
§ 371 (c)(1),
(2) Date: Sep. 27, 2016

(87) PCT Pub. No.: WO2015/150982
PCT Pub. Date: Oct. 8, 2015

(65) Prior Publication Data
US 2017/0138848 A1    May 18, 2017

(30) Foreign Application Priority Data

Mar. 31, 2014 (FR) .................................... 14 52818

(51) Int. Cl.
| | |
|---|---|
| *G01N 21/49* | (2006.01) |
| *G01N 33/04* | (2006.01) |
| *G01N 21/64* | (2006.01) |
| *G01N 21/82* | (2006.01) |
| *G01N 33/68* | (2006.01) |
| *G01N 33/487* | (2006.01) |
| *G01N 15/06* | (2006.01) |
| *G01N 15/00* | (2006.01) |

(52) U.S. Cl.
CPC ............ *G01N 21/49* (2013.01); *G01N 15/06* (2013.01); *G01N 21/6486* (2013.01); *G01N 21/82* (2013.01); *G01N 33/04* (2013.01); *G01N 33/487* (2013.01); *G01N 33/6803* (2013.01); *G01N 2015/0065* (2013.01); *G01N 2015/0693* (2013.01)

(58) Field of Classification Search
CPC .... G01N 21/49; G01N 21/6486; G01N 21/82; G01N 33/04; G01N 33/487; G01N 33/68; G01N 33/6803; G01N 33/6815; G01N 15/06; G01N 2015/0065; G01N 2015/0693; Y10T 436/25; Y10T 436/25125; Y10T 436/25375

USPC ......... 436/20, 22, 23, 86, 89, 164, 172, 174, 436/175, 177; 422/82.05, 82.08, 82.09

See application file for complete search history.

(56) References Cited

U.S. PATENT DOCUMENTS

| | | | |
|---|---|---|---|
| 3,841,834 A | 10/1974 | Gandhi et al. | |
| 3,960,493 A * | 6/1976 | Beitz ...................... | G01N 33/04 436/22 |
| 6,413,779 B1 | 7/2002 | Birlouez-Aragon | |

FOREIGN PATENT DOCUMENTS

EP      0 922 221 A1    3/1998

OTHER PUBLICATIONS

Jean et al. International Dairy Journal, vol. 16, 2006, pp. 303-315.*
Nair et al. Soft Matter, vol. 9, 2013, pp. 3815-3824.*
Guyomarc'h et al. Journal of Agricultural Food Chemistry, vol. 58, 2010, pp. 12592-12601.*
Bogomolov, A., et al., "Quantitative Determination of Fat and Total Protein in Milk Based on Visible Light Scatter," Food Chemistry 134(1):412-218, Feb. 2012.
International Search Report dated Jun. 6, 2015, issued in corresponding International Application No. PCT/IB2015/052196, filed Mar. 25, 2015, 6 pages.
Lamb, A., et al., "Optical Backscatter Method for Determining Thermal Denaturation of β-lactoglobulin and Other Whey Proteins in Milk," Journal of Dairy Science 96(3):1356-1365, Mar. 2013.
Written Opinion dated Jun. 6, 2015, issued in corresponding International Application No. PCT/IB2015/052196, filed Mar. 25, 2015, 6 pages.

* cited by examiner

*Primary Examiner* — Maureen Wallenhorst
(74) *Attorney, Agent, or Firm* — Christensen O'Connor Johnson Kindness PLLC

(57) ABSTRACT

The invention relates to a method for estimating denatured serum proteins in milk that has undergone a heat treatment. The method has the following successive steps: (a) rendering a sample of the milk transparent, (b) measuring diffusion in the transparent sample in order to deduce a first denatured serum protein (DSP) index representative of the concentration of denatured serum proteins.

19 Claims, 3 Drawing Sheets

METHOD FOR ESTIMATING DENATURED SERUM PROTEINS IN MILK

The invention relates to a method for estimating denatured serum proteins in milk. This method particularly applies to the dairy industry and more particularly to the production of cheese, yogurts, powdered milks, infant feed powders (powdered milk for infants) and other dairy products.

By <<denatured protein>> is meant a protein that has lost its original secondary and tertiary three-dimensional structure to form aggregates.

These aggregates are of varying size and type depending on whether or not caseins are contained in the medium. In the presence of caseins, serum proteins aggregate via disulfide bridges with the caseins in particular with the kappa protein. In the absence of caseins or if the caseins are insufficient in relation to the serum proteins during denaturation, the entirety or some of these proteins aggregate together.

The measurement of denatured serum proteins throughout different treatments applied to milk or derivatives, heat treatments in particular (U.H.T, pasteurisation), is fundamental in order to assess the technological quality of the milk, to standardise this quality at optimal level in terms of compromise between yield or productivity and quality, and to predict the quality of the end product this being the texture (cheese, yoghurt) or re-solubilising capability (milk powder and infant feed powder) of the product.

This is the case in cheese technology for example in which the extent of denaturation of serum proteins (ratio between denatured serum proteins and caseins) determines cheese yield. Denatured proteins will coagulate with the caseins whereas the native serum proteins will flow out of the curd.

This is the reason why cheese industrialists often apply heat treatment to milk, even enrich this milk with caseins and retentates of denatured serums to increase the percentage of milk proteins retained in the curd during coagulation. However, if the percentage of denatured serum proteins is too high there is a risk of compromising the speed and quality of coagulation, leading to a drop in production rates and loss of cheese quality in particular regarding taste and texture.

Similar problems arise for the production of yoghurts, milk and serum powders and infant feed powders.

Regarding yoghurts, the type of denaturation of the serum proteins, either on caseins or on each other, results in a very different size of the aggregates formed by the serum proteins which has a major impact on the rheology and hence the texture of the product.

Finally, for infant feed formulas, the size of the aggregates will generate problems of re-solubilisation in feed bottles.

At the present time there is no quick method to quantitate denatured proteins in milk which has undergone heat treatment (U.H.T, pasteurisation) or in a mixture of milks and/or milk derivatives of cheese milk type or in milk powders.

One laboratory technique which can be used to quantitate soluble proteins is chromatography.

Particular mention can be made of the article by V. Bonfatti et al. <<Validation of a new reversed-phase high-performance liquid chromatography method for separation and quantification of bovine milk protein genetic variants>> and the article by G. Bobe et al. <<Separation and quantification of bovine milk proteins by reversed-phase high-performance liquid chromatography>>.

Both these documents show that it is possible to quantitate first all the proteins in milk comprising caseins and serum proteins, and secondly solely the non-denatured serum proteins.

Quantitation of all the proteins is obtained by solubilising micelles of casein and possibly denatured serum proteins in a suitable denaturing buffer, the non-denatured serum proteins always remaining soluble.

The non-denatured serum proteins are quantitated by precipitating the caseins and denatured serum proteins in a suitable buffer at pH 4.6.

Using the difference between the native serum proteins and total serum proteins, quantitated separately, it is possible to determine the content of denatured serum proteins.

However, chromatography is too complex, lengthy and costly to be implemented at industrial level.

This method requires two separate quantitation operations in order to determine the quantity of denatured serum proteins.

In addition, this double quantitation leads to possible twofold error when determining the content of denatured serum proteins.

Another known technique is described in the article by I. Recio et al. <<Determination of denatured serum proteins in the casein fraction of heat-treated milk by capillary zone electrophoresis>>.

With this technique, the milk is heat treated at pH 4.6 to cause precipitation of the caseins and denatured proteins, the precipitate being solubilised. Using capillary electrophoresis, the content of denatured serum proteins and casein content are measured directly.

The conventional high pressure liquid chromatography described above can also be used, but separation is made difficult by problems relating to clogging of the chromatography column despite prior preparation of samples for re-solubilisation thereof after precipitation at pH 4.6.

Capillary electrophoresis is a technique of interest since it does not use a column. There is therefore no risk of clogging.

However, this technique is not suitable for industrial applications since it uses complex equipment, is of high cost and requires extensive know-how.

It is also possible to quantitate total and soluble serum proteins before and after heat treatment using the Kjeldahl method which is the reference method.

This method is defined by ISO standard 8668. It is based on mineralisation of the sample and colorimetric assay of nitrogen.

It can be applied to a first sample of raw milk to determine total proteins (caseins and soluble serum proteins). It can also be applied to this same sample of raw milk, after precipitation of the caseins at pH 4.6, to determine soluble serum proteins. The difference gives the casein content.

A second sample of the same raw milk is heat treated. The method is applied to this sample, after precipitation of the caseins and denatured serum proteins at pH 4.6, to obtain the quantity of serum proteins that have remained soluble. Using the difference, the amount of serum proteins denatured by heat treatment can be calculated.

These three quantitation operations allow determination of the ratio between the denatured serum proteins and caseins.

However, this requires the taking of samples at two different steps of the treatment process: hardly practical in an industrial environment. In addition, the Kjeldahl method must be carried out in a laboratory. It uses hazardous, polluting chemical products and takes several hours to carry out.

It can also be noted that the result is obtained via a succession of differences between two measurements, giving rise to major error regarding the final result, the error related to one measurement accumulating with an error on another measurement.

Furthermore, this method does not always allow the ratio be obtained between denatured serum proteins and caseins, this ratio being most useful for industrialists.

It is effectively never certain that a raw milk is truly raw milk and that there is therefore no trace of denatured proteins on the caseins.

It is therefore difficult to determine casein content with certainty using the difference between total proteins and soluble proteins.

The invention sets out to overcome the aforementioned disadvantages of the prior art, and more specifically to provide a method for the quantitation of denatured proteins in milk, that can be implemented easily and quickly (within a few minutes) even in an industrial environment.

Herein, by <<milk >> is meant both animal milk (generally cow, ewe or goat) either whole, partly or fully skimmed for direct consumption—optionally after thermisation, pasteurisation, sterilisation, concentration, drying or ultra/microfiltration—and milk having undergone diverse treatments, mixed and optionally enriched with proteins etc., intended for various industrial processing operations (production of cheese, yoghurt, concentrated or powder milk . . . ) and milk <<reconstituted>> from milk powders or infant feed powders (infant feed milk powders also containing additives such as oil, various carbohydrates, vitamins and minerals).

In the invention, by milk is also meant a cheese-making milk resulting from the mixing of various dairy ingredients, or casein-free milk i.e. a serum such as produced by microfiltration of milk (filtrate) or by draining of curd, and optionally dried after various other treatments (demineralisation, concentration . . . ).

According to the invention, said result is achieved with a method to estimate denatured serum proteins in milk that has under gone heat treatment, the method comprising the following successive steps of:

a) rendering transparent a sample of said milk;

b) measuring the scattering in said optically cleared sample to deduce therefrom a first index, DSP, representing the content of denatured serum proteins.

As part of the invention, it was evidenced that measurement of Rayleigh type scattering in the milk made transparent allows the content of denatured proteins to be estimated with good accuracy.

The inventors were therefore able to determine that the content of denatured proteins in a milk sample comprising little fat is proportional to the scatter value of this sample.

This could be due to the influence of denatured protein aggregates on Rayleigh or Mie scattering, depending on the size of these aggregates. The higher concentration of these aggregates could increase scattering in the sample.

Preferably, if the milk contains fat, the method after step a) comprises the following additional steps of:

(c) determining a second index, TP, representing the total quantity of proteins in the sample made transparent at step (a);

(d) causing precipitation of the caseins and denatured serum proteins in another sample of said milk, to obtain a precipitate and a supernatant;

(e) determining a third index, SSP, representing the soluble serum protein content of said supernatant;

(f) determining a fourth index, PD, representing protein denaturation in said supernatant; and (h) estimating the denatured serum protein content from said first, second, third and fourth indices.

The invention also concerns a method to estimate the denatured serum protein/casein ratio in milk that has been subjected to heat treatment, the method comprising the steps of:

(a) rendering transparent a sample of said milk;

(b) measuring the scattering in said optically cleared sample to deduce therefrom a first index, DSP, representing the content of denatured serum proteins;

(c) determining a second index, TP, representing the total quantity of proteins in the sample optically cleared at step (a);

(d) causing precipitation of the caseins and denatured serum proteins in another sample of said milk, to obtain a precipitate and a supernatant;

(e) determining a third index, SSP, representing the soluble serum protein content of said supernatant;

(f) determining a fourth index, PD, representing protein denaturation in said supernatant; and (i) estimating the denatured serum protein/casein ratio from said first, second, third and fourth indices.

Preferably the methods of the invention, after step (d), comprise an additional step (g) to determine a fifth index, FAST, representing the intensity of heat treatment undergone by said sample.

Advantageously, at least one of said steps (a) to (g) uses optical measurement to determine the corresponding index.

At step (c), the second index TP can be determined by measuring the fluorescence of tryptophan in the optically cleared sample.

At step (d), precipitation of the proteins can be obtained by adding a buffer having suitable ionic strength and pH to another sample of said milk.

At step (e), the third index SSP can be obtained by measuring the fluorescence of tryptophan in the transparent supernatant obtained at step (d).

At step (f), the fourth index PD can be obtained by measuring scattering in the transparent supernatant obtained at step (d).

The fifth index, FAST, can represent the content of Maillard products in the supernatant obtained at step (d).

At step (g), the fifth index FAST can be obtained by measuring the fluorescence of said Maillard products.

Finally, each of steps (h) and (i) is advantageously implemented by multilinear regression.

The invention will be better understood and other objectives, advantages and characteristics thereof will become more clearly apparent on reading the following description given in connection with the appended drawings in which.

Figure 1:
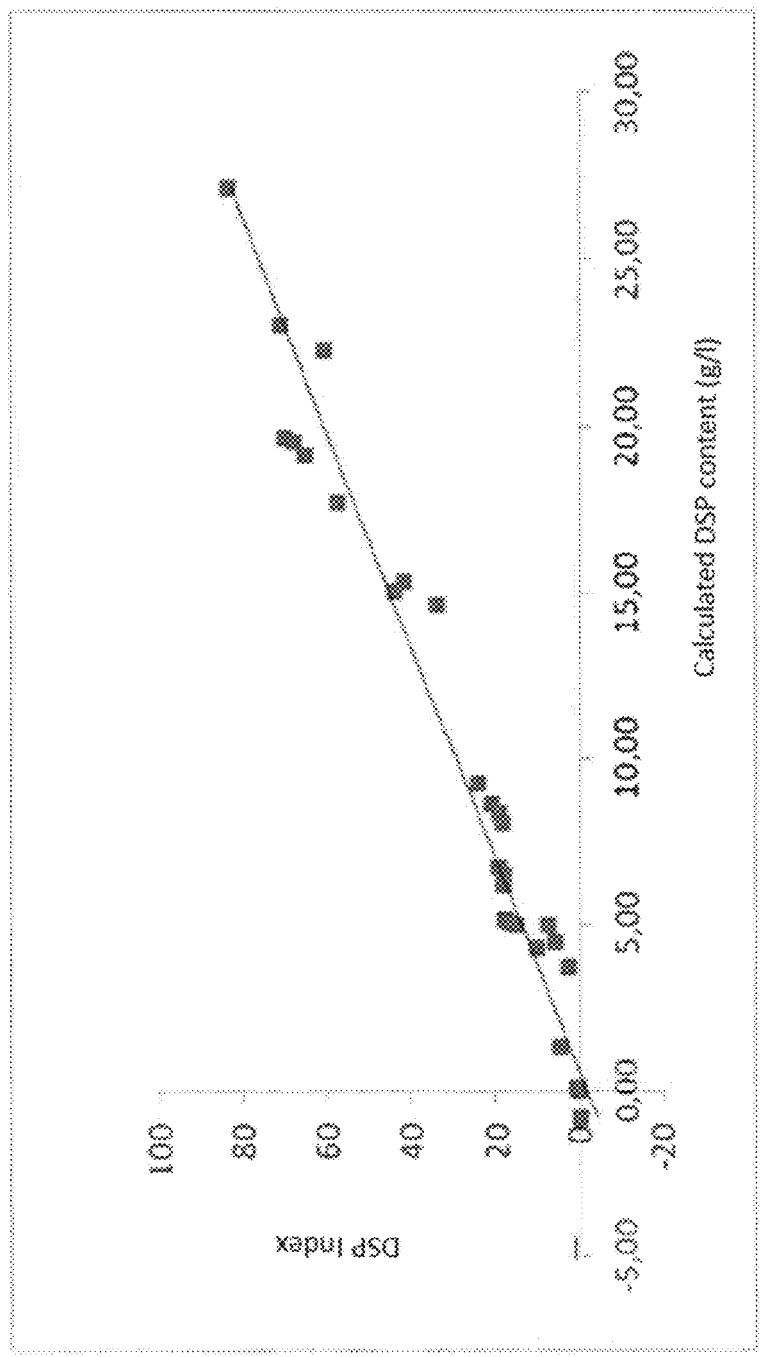
FIG. 1 is a graph illustrating the correlation existing between the denatured protein contents of different milk models not containing any fat, calculated from the constituents of the milk models (X-axis) and the values of the DSP index determined at steps (a) and (b) of the method of the invention (Y-axis)

A detailed description will now be given of the methods of the invention.

At step (a) of the method, the sample of milk to be analysed is rendered transparent.

Numerous methods are known for the optical clearing of milk. The above-mentioned articles describe such methods.

In these methods the milk sample is diluted in a proportion of 500 to 1 000, with a solution allowing solubilisation of fat by an organic solvent that is non-denaturing for proteins, and solubilisation of caseins by means of a calcium chelator maintaining bridges between the casein peptides and antioxidant agents which disrupt the disulfide bonds, and finally using a surfactant to solubilise hydrophobic proteins (casein micelles and denatured serum proteins).

A buffer, e.g. sodium or potassium phosphate containing citrate salts and a surfactant of sodium dodecylsulfate type or urea, allows chelating of the calcium, disrupting of casein micelles and partial solubilisation of the fat globules (see the article by I. Recio et al. cited above or the article by Fox et al., Journal of Dairy Science, Volume 46, Issue 4, April 1963, Pages 302-309), such as the mixture proposed in the previously cited article by Bobe et al. which contains GdnHcl (guanidine hydrochloride) and a solvent.

Other buffers can be envisaged e.g. a simple buffer comprising phosphate salts at pH 6.8 and EDTA. Said buffer allows the milk to be made transparent after dilution, but to a lesser extent than obtained with the two above-mentioned examples.

At step (b) to measure scattering, the photons reflected by the transparent milk sample are measured after prior excitation of the sample by these same photons.

It is recalled that scattering (known as Rayleigh scattering when the size of the matrix particles is close to the excitation wavelength, or Mie scattering if it is well above the wavelength) corresponds to elastic interaction (without loss of energy) between light at the wavelength under consideration and the matrix. This interaction indicates the matrix structure and in particular the size and concentration of those particles having a dimension close to the wavelength.

Various works explain this complex phenomenon difficult to quantitate in complex, heterogeneous matrixes:

C. F. Bohren and D. R. Huffman. Absorption and scattering of light by small particles. John Wiley & Sons, New York, 1983, Light scattering by small particles. By H. C, van de Hulst. New York (John Wiley and Sons), London (Chapman and Hall), 1957, Wave Propagation and Scattering in Random Media, Akira Ishimaru, January 1999, Wiley-IEEE Press.

Therefore, the measurement of scattering in a simple solution of serum proteins gives a direct, proportional index of the concentration of denatured proteins (DSP index) due to the formation of aggregates of denatured proteins having a much larger size than the unit soluble proteins. Scattering in conventional mode can be used over a large range, from near to far UV including in the visible. However, sensitivity is higher in UV.

This step (a) to obtain transparency is first performed on milk not containing any fat.

More specifically, the milks used are model milks reconstituted in the laboratory by associating serum powder, milk powder and water, this reconstituted milk having been subjected to heat treatment. In practice, several model milks were prepared having varying contents of serum and milk powder to obtain different values of total serum protein content and of the total serum protein to casein ratio. Heat treatment allows the production of denatured serum proteins in varying concentrations.

FIG. 1 is a graph illustrating the correlation existing between the denatured protein contents of the different milk models—calculated for each milk model by the difference between the total serum proteins used in the milk model and the soluble serum protein content after heat treatment determined using the Kjeldahl method (X-axis)—and the values of the DSP index determined at steps (a) and (b) of the method of the invention (Y-axis).

FIG. 1 shows that excellent regression is observed between measurement of scatter in conventional mode (DSP index) representing the content of denatured serum proteins (DSP), and the measurement calculated directly for the milk models as indicated above.

The coefficient of correlation is 0.98.

The accuracy obtained is better the lower the fat content.

The size of fat globules modifies scattering and hence also the relationship between the concentration of denatured protein aggregate and scattering.

It was found that other measurements allow estimation of the content of denatured serum proteins even in the presence of fat-containing milk.

A description will now be given of these different measurements.

The objective of one additional measurement is to determine a second index, TP, representing the total amount of proteins in the optically cleared sample. This determination can be performed by measuring the fluorescence of tryptophan in the cleared sample by conducting step (c) that is carried out after step (a).

This measurement of tryptophan fluorescence can be performed using the method described in the above-cited article by Fox et al.

The principle of this method is to consider that, if the medium is transparent, the Beer Lambert law applies quantitatively relating the fluorescence of a molecule, here tryptophan (Trp), with the concentration of proteins carrying this amino acid.

With respect to milk, all the proteins contain tryptophan, which means that this method can be used to determine the total proteins contained in the sample.

With this measurement it is possible to estimate the total quantity of proteins in the optically cleared sample.

The purpose of another additional measurement is to determine a third index, SSP, representing the content of soluble serum proteins.

For this measurement the following steps are performed:

(d) preparing another sample of said milk to which is added a buffer of suitable ionic strength and pH to obtain first a precipitate of caseins and proteins denatured by said heat treatment and secondly a transparent supernatant containing serum proteins still remaining soluble;

(e) determining the tryptophan content in said transparent supernatant.

Both steps (d) and (e) are described and illustrated in document EP-0 922 221.

Preferably, the tryptophan contained in the supernatant is determined via its fluorescence; for example, measurement is carried out at an excitation wavelength of 290 nm and an emission wavelength of between 330 and 350 nm to obtain maximum sensitivity. Quantitation of tryptophan could also be determined by its UV absorption.

Document EP-0 922 221 showed that tryptophan fluorescence in the transparent supernatant is a quick method of measuring the concentration of scarcely denatured soluble proteins and that it very strongly correlates with the quantitation of proteins (Kjeldahl or Buiret colorimetric method; r=0.99).

Steps (d) and (e) therefore allow estimation of the amount of soluble (or non-denatured) serum proteins in the supernatant.

A further additional measurement is the determination of a fourth index representing denaturation of the proteins in the supernatant obtained at step (d).

This determination is carried out by measuring scatter in the supernatant, corresponding to step (f).

This step (f) gives an indication on the denaturing of the proteins. It gives the mean size of the protein particles in the supernatant of soluble serum proteins. Even if these proteins have still not been made insoluble, they underwent a first structural modification during heat treatment and in particular they formed small aggregates seen through the scattering.

This step is performed on the supernatant obtained at step (d).

At this step, scattering is measured at 280 nm (for excitation at 280 nm).

Steps (a) to (f) have been described in succession. However, steps (a), (b) and (c) firstly and steps (d), (e) and (f) secondly can be performed in parallel or in any order.

The purpose of a final additional measurement is to define a fifth index, FAST, representing the Maillard reaction on the proteins of the supernatant obtained at step (d), this reaction being highly dependent on the heat load applied to the milk.

It may entail quantitation of the fluorescent by-products derived from the advanced Maillard reaction and contained in said supernatant.

This additional step (g) therefore allows determination of a global heat index indicating the type of heat treatment undergone by the milk and the quality of this treatment.

It is described and illustrated in document EP-0 922 221.

This index gives information on the heat load absorbed by the milk and hence on the thermal denaturation of the serum proteins, to determine the content of soluble serum proteins.

This step (g) can be performed after step (d) in parallel with steps (e) and (f), or before or after these steps (e) and (f).

Figure 2:
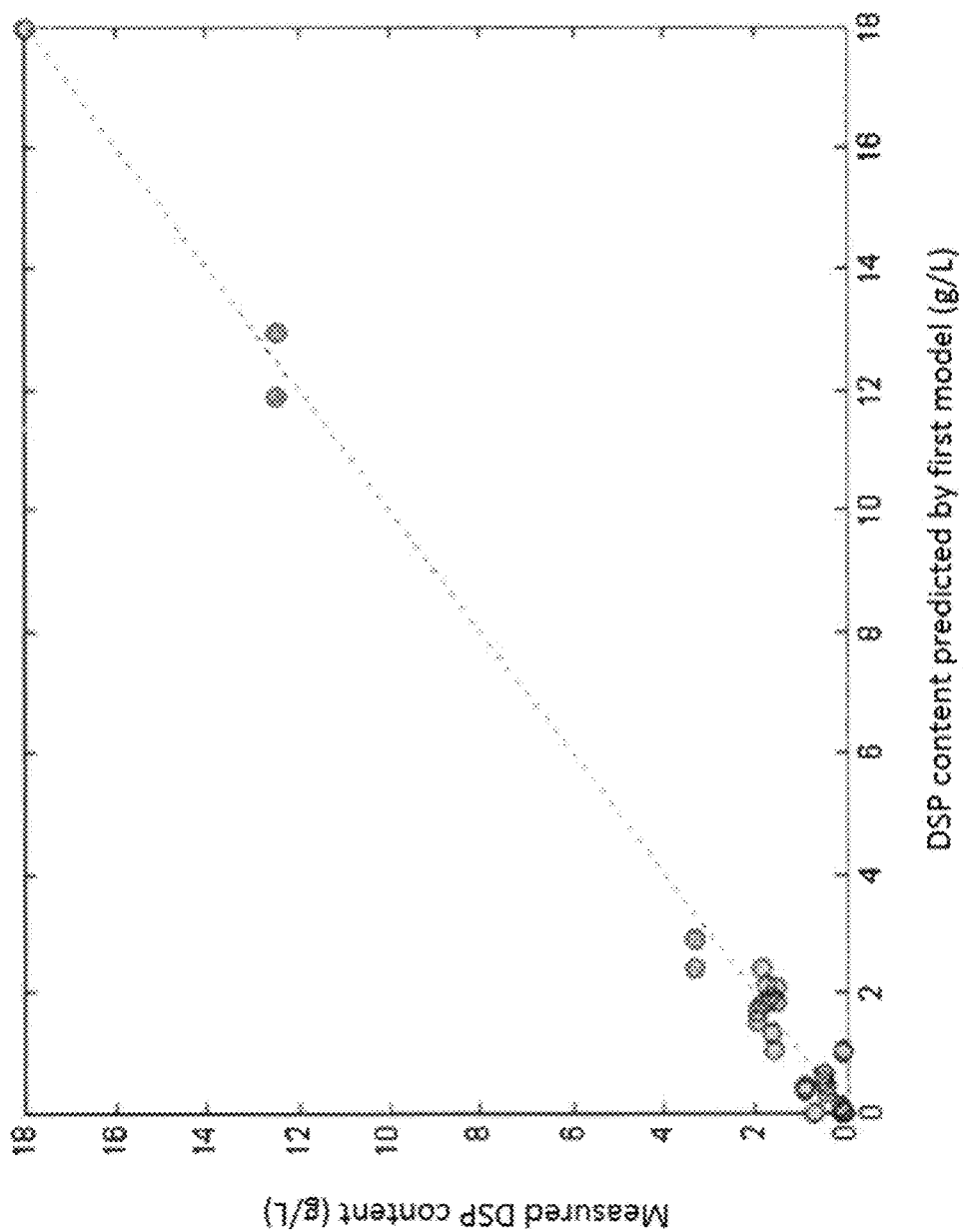
FIG. 2 is a graph illustrating the regression between the denatured serum protein contents (DSP) measured by capillary electrophoresis (Y-axis) and predicted at steps (a) to (g) of the method of the invention (X-axis) for different industrial cheese milks containing fat.

FIG. 2 is a graph illustrating the regression between the content of denatured serum proteins (DSP) as measured by capillary electrophoresis and predicted by steps (a) to (g) of the method of the invention.

Capillary electrophoresis measurements and steps (a) to (f) of the method of the invention were performed on samples supplied by industrial partners and corresponding to industrial cheese milks, comprising skimmed milk, microfiltration retentate enriched with caseins, optionally serum retentate heated to allow denaturing thereof, milk fat and finally a mixture of mineral salts, calcium in particular.

Therefore, first the milk proteins were analysed using the technique described by Recio and Olieman: after solubilising the caseins and denatured proteins obtained by precipitation of the heated milk sample at pH 4.6, the sample was analysed by capillary electrophoresis to determine serum proteins and caseins. Analysis of the precipitation supernatant allowed quantitation of the soluble serum proteins.

In parallel, on these same samples, steps (a) to (g) of the method of the invention were performed.

Therefore, these samples were rendered transparent (step (a)) and conventional scatter measurement (step (b)) was conducted to determine a DSP index representing the content of denatured serum proteins, as well as measurement of tryptophan fluorescence (step (c)) to determine an index TP representing the total quantity of proteins.

In addition the crude samples were treated to isolate the soluble serum proteins (step (d)) for analysis thereof by determining the tryptophan contained in the supernatant via fluorescence (step (e)) to obtain an index SSP representing the content of soluble serum proteins in the supernatant, for measurement of scattering in the supernatant (step (f)) to determine an index PD to determine protein denaturation, and finally for determination of a global heat index (FAST index) by quantitating in the supernatant the fluorescence by-products derived from the advanced Maillard reaction (step (g)).

In practice, 500 µl of cheese milk are used that are diluted in 10 ml of water. These are mixed together and 250 µl of diluted milk are taken that are diluted in 10 ml of optical clearing buffer. After 5 minutes the mixture is transparent and it is possible to measure scattering and fluorescence at the maximum emission length of tryptophan (337 nm), after excitation at 280 nm. The conversion of tryptophan fluorescence to serum protein concentration is obtained by means of a standard milk sample treated in the same manner and having a known concentration of total proteins (determination using the reference Kjeldahl method). Scattering is also measured at 280 nm, after excitation at 280 nm.

In parallel, 1 ml of cheese milk is taken and precipitated with 50 ml of buffer at pH 4.6. After filtration, a transparent solution is obtained solely containing the soluble serum proteins that are analysed at 337 nm, after excitation at 280 nm, to obtain the protein concentration thereof. Scattering is also measured at 280 nm, and the concentration of Maillard products at 350 nm excitation and 430 nm emission. The conversion of tryptophan fluorescence to serum protein concentration is obtained using a soluble serum protein standard of known concentration (determination using the reference Kjeldahl method).

Excellent regression was observed between the measurements performed by capillary electrophoresis and the five indices determined at steps (a) to (g) of the method of the invention, regarding the quantity of denatured serum proteins. The coefficient of correlation was 0.99 and the model error was 0.49 g/L over a content distribution of between 0 and 18 g/L.

A first multilinear regression model was therefore constructed between the quantity of denatured proteins, determined by the electrophoretic method, and a linear combination of the various measurements performed at steps (a) to (g) of the method of the invention.

Regression of good quality was obtained with a calibration error given by the RMSEC indicator (Root Mean Square Error of Calibration) close to the error of the reference method.

The influence of the different indices on error of the result obtained with the constructed model and on the coefficient of correlation is given in Table 1 below.

The complete model is based on the five indices respectively given by steps (a) to (g): DSP index, TP index, SSP index, PD index and FAST index.

The model corresponding to the milks and measurements in FIG. 2 is defined by:

$$\text{DSP content(g/L)} = \text{Exp}(-6.96683070 + 0.11696939 \cdot \text{SSP index} + 0.09522332 \cdot \text{FAST index} + 0.01943347 \cdot \text{TP index} + 0.00110096 \cdot \text{PD index} + 0.06505071 \cdot \text{DSP index}).$$

Evidently, for other milk components, the coefficients of the model must be slightly adapted.

The error value (RMSEC) and value of the coefficients of correlation ($R^2$) are given on the first line of Table 1.

The following lines give these same values when the model is only based on four of these five indices.

TABLE 1

| Model | RMSEC | $R^2$ |
|---|---|---|
| Complete | 0.49 | 0-99 |
| Without SSP index | 0.85 | 0.98 |
| Without FAST index | 0.48 | 0.99 |
| Without TP index | 0.88 | 0.98 |
| Without PD index | 0.87 | 0.98 |
| Without DSP index | 1.23 | 0.97 |

It shows that the FAST index, relating to heat load, has a non-significant impact on the model.

The model can therefore only take into account those indices obtained at steps (a) to (f) of the method i.e. the indices SSP, TP, PD and DSP.

Table 1 shows that it is the DSP index which has a predominant role in this first model, even if the other indices bring a significant improvement in the quality of the model and hence in the accuracy of prediction.

As previously indicated, it is of interest to determine the ratio between the denatured serum proteins and the caseins, an indicator that is useful for industrialists. The ratio is effectively a good predictor of the technological quality of cheese milk (coagulation time, drainage rate and curd texture) and of cheese yield. Also, steps (a) to (e) allow estimation of casein content, which corresponds to the total quantity of proteins (step (c)) from which are subtracted the quantity of denatured serum proteins (steps (a) and (b)) and the quantity of non-denatured serum proteins (steps (d) and (e)).

It is therefore understood that steps (a) to (e) will be useful to estimate this ratio.

Figure 3:
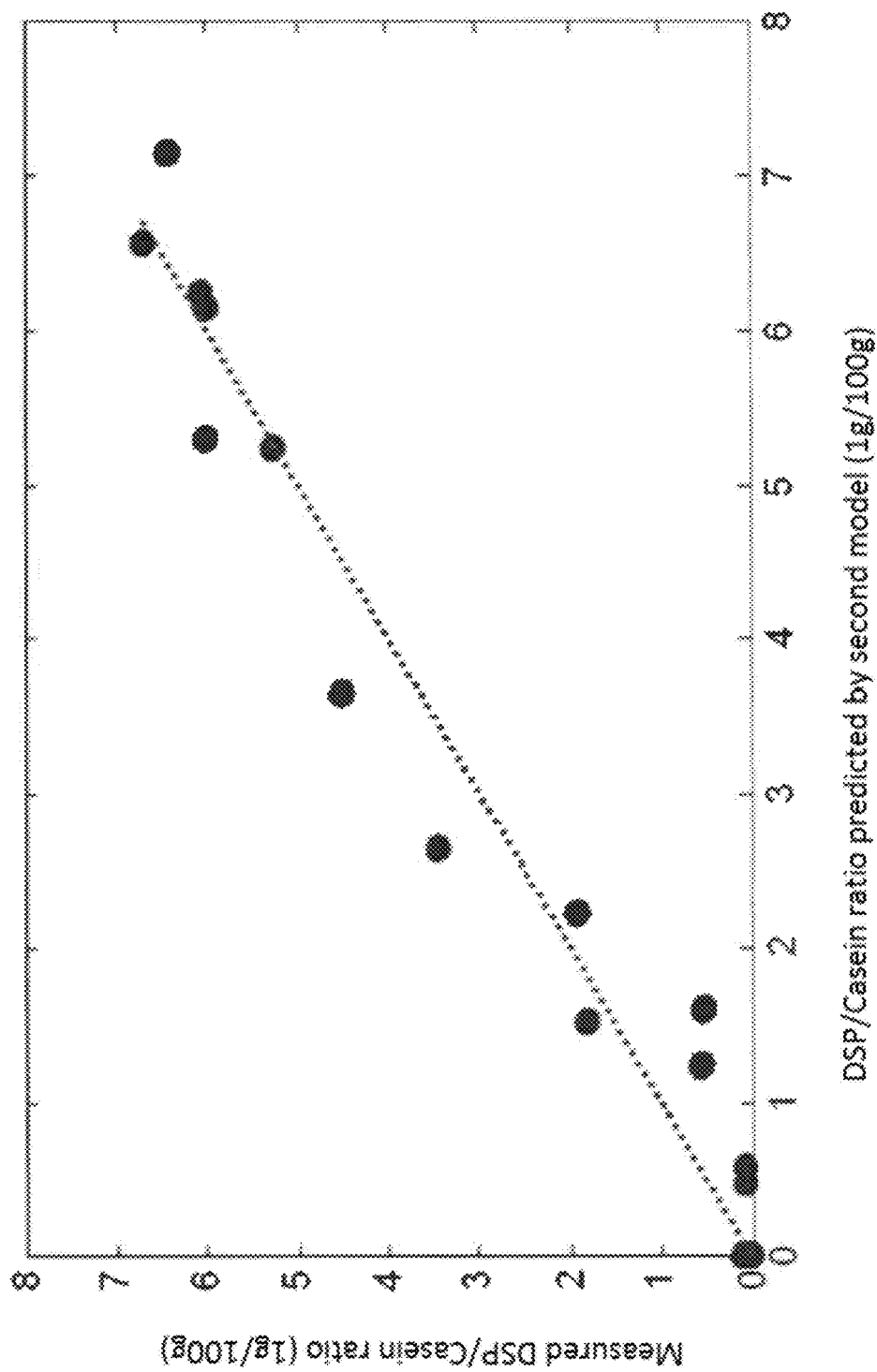
FIG. 3 is a graph illustrating the regression between the denatured serum protein content (DSP) as a percentage relative to the casein content in these same industrial cheese milks measured by capillary electrophoresis (Y-axis) and predicted by steps (a) to (g) of the method of the invention (X-axis).

FIG. 3 is a graph illustrating the regression between the content of denatured serum proteins (DSP) as a percentage relative to the casein content, as measured by capillary electrophoresis and predicted by steps (a) to (g) of the method of the invention.

Measurements by capillary electrophoresis and steps (a) to (f) of the method of the invention were performed on samples supplied by industrial partners and correspond to standardised cheese milks comprising skimmed milk, microfiltration retentate enriched with caseins, optimally serum retentate heated for denaturation thereof, milk fat and finally a mixture of mineral salts, calcium in particular. These were the same milks as used for the measurements corresponding to FIG. 2.

These measurements by capillary electrophoresis and steps (a) to (g) were conducted as previously explained and will not be further detailed.

FIG. 3 shows excellent regression between the measurements performed by capillary electrophoresis and the five indices determined at steps (a) to (g) of the method of the invention regarding the denatured serum protein/casein ratio (DSP).

The coefficient of correlation $R^2$ was 0.98 and the model error was about 3%.

A second multilinear regression model was then constructed between the DSP/casein ratio as determined by the electrophoretic method and by the different indices obtained at steps (a) to (g) of the method of the invention.

The model corresponding to the milks and measurements of FIG. 3 is defined by:

DSP/Casein ratio=Exp(−123.151918+1.60789852·TP index+0.07233199·PD index−6.43110855·DSP index−0.81489076·SSP index−0.02069923·FAST index).

Evidently for other milk compositions the coefficients of the model must be slightly adapted.

Regression of good quality was obtained with a calibration error given by the RMSEC indicator close to the error of the reference method.

The influence of the different indices on the error of result obtained with the constructed model and on the coefficient of correlation is given in Table 2 below:

TABLE 2

| | RMSEC | $R^2$ |
|---|---|---|
| All variables | 0.68 | 0.98 |
| Without SSP index | 1.33 | 0.91 |
| Without FAST index | 1.09 | 0.94 |
| Without TP index | 1.25 | 0.92 |
| Without PD index | 1.53 | 0.89 |
| Without DSP index | 1.32 | 0.91 |

This Table 2 shows that all the indices are significant but that the FAST index brings the least important contribution to the model. However, it allows lowering of the model error from 1.09 to 0.68 and an increase in the value of $R^2$ from 0.94 to 0.98.

In practice, the model may solely take into account the indices obtained at steps (a) to (f) of the method, i.e. the indices SSP, TP, PD and DSP.

Table 2 shows that it is the PD index which plays a predominant role in this second model, followed by the DSP and SSP indices.

Therefore, with the invention it is possible to estimate the content of denatured serum proteins in milk whether or not the milk contains fat. It also allows estimation of the denatured serum protein/casein ratio in a milk irrespective of type.

In addition, the methods of the invention can be used to estimate these magnitudes using steps that are quick and easy to implement and which are of low cost compared with known methods.

For example, analysis of milk performed by capillary electrophoresis requires the transmitting of samples to an outside laboratory, and a wait of several days to obtain results entailing costs of several hundred euros.

Analysis performed using a method of the invention can be conducted on site, the results are therefore known immediately (5 minutes) and costs are in the region of 15 euros.

In addition, contrary to known methods that are laboratory methods, the methods of the invention are industrial methods.

The invention claimed is:

1. A method to estimate denatured serum proteins in milk having undergone heat treatment, the method comprising the successive steps of:
   (a) rendering transparent a sample of said milk;
   (b) measuring a scattering in said transparent sample to deduce a first index, DSP, representing a content of denatured serum proteins;
   (c) determining a second index, TP, representing a total quantity of proteins in the transparent sample cleared at step (a);
   (d) causing precipitation of caseins and denatured serum proteins in another sample of said milk, to obtain a precipitate and a supernatant;

(e) determining a third index, SSP, representing a content of soluble serum proteins in said supernatant;
(f) determining a fourth index, PD, representing protein denaturation in said supernatant; and
(h) estimating a content of denatured serum proteins with a first model defined by $$\text{DSP content(g/L)} = \text{Exp}(x1 + x2 \cdot \text{SSP index} + x3 \cdot \text{TP index} + x4 \cdot \text{PD index} + x5 \cdot \text{DSP index}),$$

wherein x1, x2, x3, x4 and x5 are first model coefficients obtained by constructing a first multilinear regression between a content of denatured serum proteins measured by a capillary electrophoresis in said milk and a linear combination of the said first, second, third, and fourth indices determined at steps (a) to (f).

2. The method according to claim 1 comprising, after step (f), an additional step (g) whereby a fifth index, FAST, is determined representing an intensity of heat treatment undergone by said sample and the content of denatured serum proteins is estimated at step (h) with a third model defined by $$\text{DSP content(g/L)} = \text{Exp}(x1 + x2 \cdot \text{SSP index} + x3 \cdot \text{TP index} + x4 \cdot \text{PD index} + x5 \cdot \text{DSP index} + x6 \cdot \text{FAST index}),$$

wherein x1, x2, x3, x4, x5 and x6 are third model coefficients obtained by constructing a third multilinear regression between a content of denatured serum proteins measured by a capillary electrophoresis in said milk and a linear combination of the said first, second, third, fourth and fifth indices determined at steps (a) to (g).

3. The method according to claim 2, wherein at least one of said steps (a) to (g) uses optical measurement to determine the corresponding index.

4. The method according to claim 2, wherein the fifth index FAST represents a Maillard product content of the supernatant obtained at step (d).

5. The method according to claim 4, wherein at step (g) the fifth index FAST is obtained by measuring a fluorescence of said Maillard products.

6. The method according to claim 1, wherein at step (c) the second index TP is determined by measuring a fluorescence of tryptophan in the transparent sample.

7. The method according to claim 1, wherein at step (d) precipitation of the proteins is obtained by adding a denaturing buffer to another sample of said milk, said denaturing buffer having ionic strength and pH suitable for proteins in the supernatant to always remain soluble.

8. The method according to claim 1, wherein at step (e) the third index SSP is obtained by measuring a fluorescence of tryptophan in the supernatant obtained at step (d).

9. The method according to claim 1, wherein at step (f) the fourth index PD is obtained by measuring scattering in the supernatant obtained at step (d).

10. The method according to claim 1, wherein step (h) is implemented by multilinear regression.

11. A method to estimate a denatured serum protein/casein ratio in milk that has been subjected to heat treatment, the method comprising the steps of:
(a) rendering transparent a sample of said milk;
(b) measuring a scattering in said transparent sample to deduce therefrom a first index, DSP, representing a content of denatured serum proteins;
(c) determining a second index, TP, representing a total quantity of proteins in the sample optically cleared at step (a);
(d) causing precipitation of caseins and denatured serum proteins in another sample of said milk, to obtain a precipitate and a supernatant;
(e) determining a third index, SSP, representing a content of soluble serum proteins in said supernatant;
(f) determining a fourth index, PD, representing protein denaturation in said supernatant; and
(i) estimating a denatured serum protein/casein ratio with a second model defined by $$\text{DSP/Casein ratio} = \text{Exp}(y1 + y2 \cdot \text{TP index} + y3 \cdot \text{PD index} - y4 \cdot \text{DSP index} - y5 \cdot \text{SSP index}),$$

wherein y1, y2, y3, y4 and y5 are second model coefficients obtained by constructing a second multilinear regression between a content of denatured serum proteins measured by a capillary electrophoresis in said milk and a linear combination of the said first, second, third and fourth indices.

12. The method according to claim 11, wherein step (i) is implemented by multilinear regression.

13. The method according to claim 11 comprising, after step (f), an additional step (g) whereby a fifth index, FAST, is determined representing an intensity of heat treatment undergone by said sample.

14. The method according to claim 13, wherein at least one of said steps (a) to (g) uses optical measurement to determine the corresponding index.

15. The method according to claim 13, wherein the fifth index FAST represents a Maillard product content of the supernatant obtained at step (d).

16. The method according to claim 11, wherein at step (c) the second index TP is determined by measuring a fluorescence of tryptophan in the transparent sample.

17. The method according to claim 11, wherein at step (d) precipitation of the proteins is obtained by adding a denaturing buffer to another sample of said milk, said denaturing buffer having ionic strength and pH suitable for the proteins in the supernatant to always remain soluble.

18. The method according to claim 11, wherein at step (e) the third index SSP is obtained by measuring a fluorescence of tryptophan in the supernatant obtained at step (d).

19. The method according to claim 11, wherein at step (f) the fourth index PD is obtained by measuring scattering in the supernatant obtained at step (d).

* * * * *